United States Patent
Wenzel et al.

(10) Patent No.: US 6,668,181 B2
(45) Date of Patent: *Dec. 23, 2003

(54) METHOD FOR QUANTIFICATION OF STRATUM CORNEUM HYDRATION USING DIFFUSE REFLECTANCE SPECTROSCOPY

(75) Inventors: Brian J. Wenzel, Cave Creek, AZ (US); Stephen L. Monfre, Gilbert, AZ (US); Timothy L. Ruchti, Gilbert, AZ (US); Ken Meissner, Gilbert, AZ (US); Frank Grochocki, Chandler, AZ (US); Thomas Blank, Chandler, AZ (US); Jessica Rennert, Scottsdale, AZ (US)

(73) Assignee: Sensys Medical, Inc., Chandler, AZ (US)

(*) Notice: Subject to any disclaimer, the term of this patent is extended or adjusted under 35 U.S.C. 154(b) by 0 days.

This patent is subject to a terminal disclaimer.

(21) Appl. No.: 10/161,197

(22) Filed: May 31, 2002

(65) Prior Publication Data

US 2002/0183602 A1 Dec. 5, 2002

Related U.S. Application Data

(63) Continuation of application No. 09/669,781, filed on Sep. 25, 2000, now Pat. No. 6,442,408.

(51) Int. Cl.$^7$ ................................................ A61B 5/00
(52) U.S. Cl. .................... 600/310; 600/473; 250/339.1; 250/341.8
(58) Field of Search .................. 600/310, 322, 600/473, 475; 356/303; 250/339.01, 339.07, 339.09, 339.1, 339.11, 340, 341.5, 341.8

(56) References Cited

U.S. PATENT DOCUMENTS 6,442,408 B1 * 8/2002 Wenzel et al. .............. 600/310

FOREIGN PATENT DOCUMENTS

CA        2210791    * 1/1999

* cited by examiner

Primary Examiner—Eric F. Winakur
(74) Attorney, Agent, or Firm—Glenn Patent Group; Michael A. Glenn; Christopher Peil

(57) ABSTRACT

An apparatus and method for non-invasively quantifying the hydration of the stratum corneum of a living subject utilizes in vivo spectral measurements made by irradiating skin tissue with near infrared (NIR) light. The apparatus includes a spectroscopic instrument in conjunction with a subject interface. The resulting NIR absorption spectra are passed to an analyzer for further processing, which includes detecting and eliminating invalid spectral measurements, and preprocessing to increase the signal-to-noise ratio. Finally, a calibration model developed from an exemplary set of measurements is applied to predict the SC hydration for the sample. The method of SC hydration measurement provides additional information about primary sources of systematic tissue variability, namely, the water content of the epidermal layer of skin and the penetration depth of the incident light. The stratum corneum hydration measurement is therefore suitable for further spectral analysis and the quantification of biological and chemical compounds, such as blood analytes.

28 Claims, 7 Drawing Sheets

METHOD FOR QUANTIFICATION OF STRATUM CORNEUM HYDRATION USING DIFFUSE REFLECTANCE SPECTROSCOPY

CROSS REFERENCE TO RELATED APPLICATION

This application is a Continuation of U.S. patent application Ser. No. 09/669,781, filed on Sep. 25, 2000, now U.S. Pat. No. 6,442,408 B1.

BACKGROUND OF THE INVENTION

1. Field of the Invention

The invention relates to the use of spectroscopy to characterize living tissue. More particularly, the invention relates to an apparatus and method for quantifying hydration of the stratum corneum of a living subject non-invasively, based on irradiation of the skin tissue with near infrared light energy.

2. Description of Related Art

Near infrared (NIR) tissue spectroscopy is a promising non-invasive technology that bases measurements on the irradiation of a tissue site with NIR energy in the 700–2500 nanometer wavelength range. The energy is focused onto an area of the skin and propagates according to the scattering and absorption properties of the skin tissue. Therefore, the reflected or transmitted energy that escapes and is detected provides information about the tissue volume that is encountered. Specifically, the attenuation of the light energy at each wavelength is a function of the structural properties and chemical composition of the tissue. Tissue layers, each containing a unique heterogeneous particulate distribution, affect light absorbance through scattering. Chemical components such as water, protein, fat and blood analytes absorb light proportionally to their concentration through unique absorption profiles or signatures. The measurement of tissue properties, characteristics or composition is based on detecting the magnitude of light attenuation resulting from its respective scattering and/or absorption properties.

Stratum Corneum Hydration Measurement

The quantification of hydration of the stratum corneum has commercial benefits in certain industries for monitoring skin condition and for attaining a better understanding of how hydration affects the stratum corneum. The current method of measuring the hydration of the stratum non-invasively is based on the electrical characteristics of the stratum corneum. The technology measures the capacitance, admittance, impedance, or susceptance of the stratum corneum.

Spectroscopic approaches to measuring hydration of the stratum corneum have been explored. See, for example, R. Potts, D. Guzek, R. Harris, J. McKie, *A Noninvasive, In Vivo Technique to Quantitatively Measure Water Concentration of the Stratum Corneum Using Attenuated Total-Reflectance Infrared Spectroscopy, Archives of Dermatological Research*, Springer-Verlag, Vol. 277, (1985). Potts, et al. performed a variety of in vitro experiments using Attenuated Total Reflectance (ATR) spectroscopy in the infrared region of light, and determined that hydration of the skin was highly correlated (0.99) to the ambient humidity. He developed a variety of preprocessing techniques like the protein ratio and the moisture factor to measure the hydration of the stratum. He concluded that water content in the stratum corneum could be measured in vitro using ATR infrared spectroscopy. The Potts teachings however are directed to an in vitro method and are therefore unsuited to non-invasive, in vivo measurements.

Martin did a series of experiments related to in vivo measurement using diffuse reflectance near infrared spectroscopy. See K. Martin, *Direct Measurement of Moisture in Skin by NIR Spectroscopy, Journal of Society of Cosmetic Chemists*, Vol. 44 (1993). Martin's work lead to the finding that three different types of water may be detected in the spectra of skin. The different types of water were found in the combination region (1058–1950 nm) using the second derivative of the spectrum; second derivative intensities were found to correlate with ambient humidity levels. It was found that the bulk water of the stratum corneum correlates most directly with ambient humidity. Bulk water was water that mostly resembled that of regular water and was not bound to any protein. It was also found that the primary hydration water correlated the least with ambient humidity.

Martin's further work investigated the use of measuring sites at a variety of body locations having skin of varying thickness. See K. Martin, *In Vivo Measurements of Water in Skin by Near Infrared Reflectance, Applied Spectroscopy*, Vol. 52(7)(1998). While a higher standard deviation was noted, the previous correlations with different water types in the skin were confirmed. Additionally, light scattering by the skin was found to decrease with increasing hydration. The Martin teachings, however, do not address the persistent problem in the art of compensating for structural and physiological variation between individuals or variation over time within the same individual.

Blood Analyte Prediction

While non-invasive prediction of blood analytes, such as blood glucose concentration, has been pursued through NIR spectroscopy, the reported success and product viability has been limited by the lack of a system for compensating for structural variations between individuals that produce dramatic changes in the optical properties of the tissue sample. For example, see O. Khalil, *Spectroscopic and clinical aspects of non-invasive glucose measurements, Clin Chem.* Vol. 45, pp 165–77 (1999) or J. Roe, B. Smoller, *Bloodless Glucose Measurements, Critical Reviews in Therapeutic Drug Carrier Systems*. Vol. 15, no. 3, pp. 199–241, 1998. These differences are largely anatomical and provide distinct systematic spectral absorbance features or patterns that can be related directly to specific characteristics such as dermal thickness, protein levels and hydration. While the absorbance features are repeatable within a subject, over a population of subjects they produce confounding nonlinear spectral variation. Therefore, differences between subjects are a significant obstacle to the non-invasive measurement of blood analytes through NIR spectral absorbance.

The related U.S. Patent Application, S. Malin, T. Ruchti, *An intelligent system for noninvasive blood analyte prediction*, U.S. patent application Ser. No. 09/359,191 (Jul. 22, 1999) discloses an apparatus and procedure for substantially reducing this problem by classifying subjects according to major skin tissue characteristics prior to blood analyte prediction. The selected characteristics are representative of the actual tissue volume irradiated and the amount of the target analyte that is sampled. By grouping individuals according to the similarity of spectral characteristics representing the tissue structure, the nonlinear variation described above is reduced and prediction of blood analytes becomes more accurate.

SUMMARY OF THE INVENTION

The present invention provides a novel apparatus and related procedures for the quantification of hydration of the stratum corneum through NIR tissue spectroscopy having particular benefit in several areas, including tissue state evaluation and blood analyte prediction. The invention utilizes NIR diffuse reflectance to measure the hydration of the stratum corneum. A spectroscopic apparatus in conjunction with an optical subject interface is used to measure tissue properties and characteristics non-invasively that are manifested spectrally and vary systematically according to the hydration of the subject's stratum corneum.

The procedure for quantifying stratum corneum hydration involves a calibration model that is empirically derived from a set of exemplary samples consisting of NIR tissue measurements and corresponding independent measurements made with a corneometer. The model is a set of parameters and computer generated code that is implemented to predict the hydration of the subject's stratum corneum. The general procedure involves the steps of taking spectral measurements, typically in the near IR region of 700 to 2500 nm; detecting outliers, invalid measurements resulting from poor sampling technique, or instrument problems, or a subject outside of the calibration set; preprocessing, in which the spectral measurements are subjected to various operations that attenuate noise and instrumental variation; and prediction, in which the previously mentioned calibration model is applied to arrive at an estimation of the hydration of the subject's stratum corneum.

DETAILED DESCRIPTION

Figure 1:
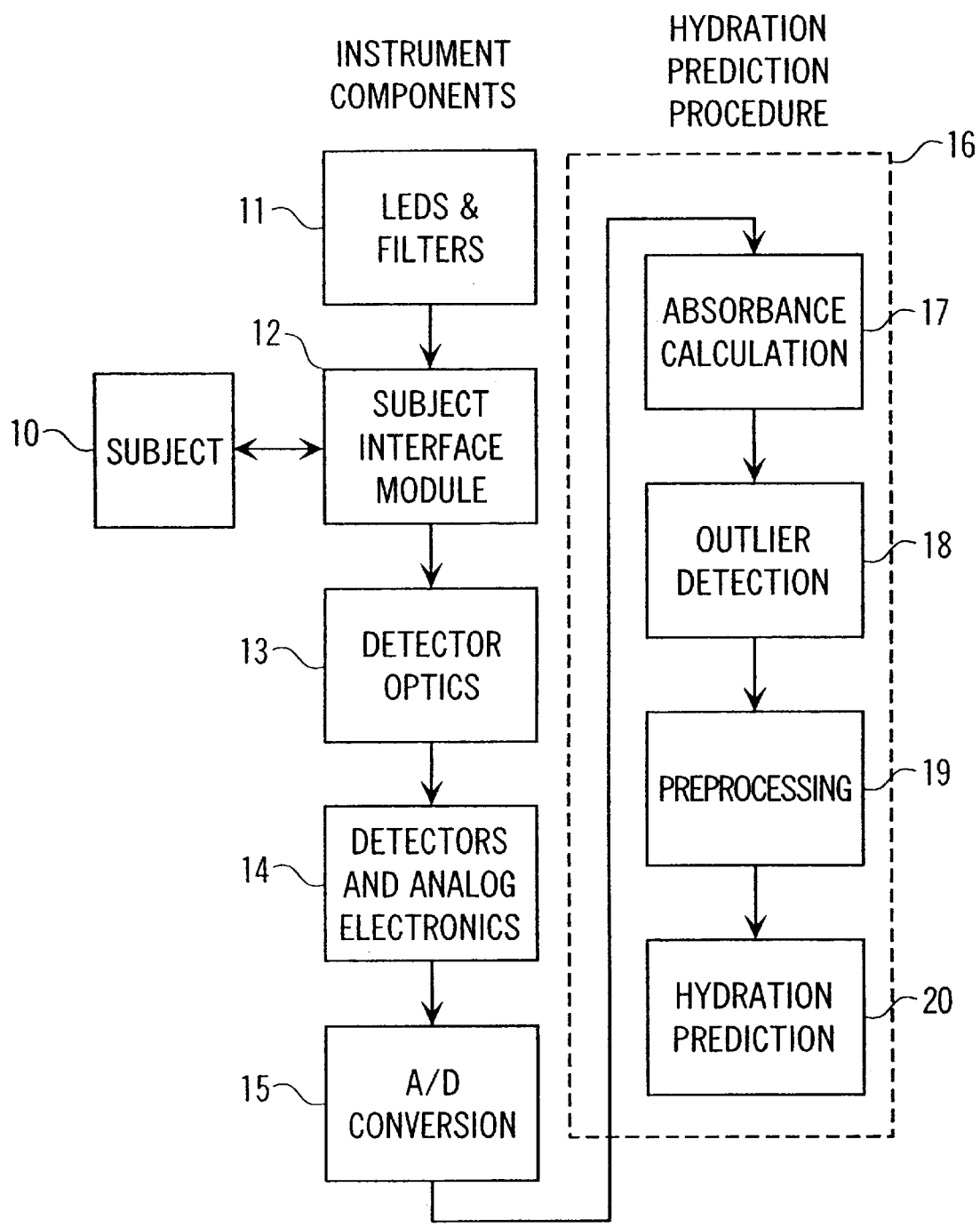
FIG. 1 provides a block diagram of a system for predicting stratum corneum hydration, according to the invention.

The system for quantifying the Stratum Corneum hydration non-invasively provides an apparatus for measuring the near infrared absorption by tissue irradiated with near infrared energy and a procedure for determining hydration of the Stratum Corneum. Although the invented apparatus and procedure are described herein with respect to quantifying hydration of the Stratum Corneum, one skilled in the art will recognize that the invention has application in quantifying hydration of other forms of tissue.

Hydration Prediction Apparatus

The apparatus includes an energy source 11, one or more sensor elements, an interface 12 to the subject 10, a wavelength selection device and an analyzer. The source generates and transmits near-infrared energy in the wavelength range 700–2500 nanometers and consists of a device such as an LED array 11 or a quartz halogen lamp. The sensing elements are detectors 14, which are responsive to the targeted wavelengths. The method of wavelength separation includes a monochromator, an interferometer or successive illumination through the elements of an LED array 11. The interface to the subject comprises a means of transmitting energy from the source 11 to the target skin tissue measurement site and includes, for example a light pipe, fiber-optic probes, a lens system or a light directing mirror system. Energy is collected from the surrounding tissue areas in reflectance mode at an optimally determined distance(s) through the use of detectors 13 or fiber optics. Alternately, energy is collected in a transmission mode through a skin fold, ear lobe, finger or other extremity. The collected light is converted to a voltage 14 and sampled through an analog-to-digital converter 15 for analysis on a data processing system.

Figure 4:
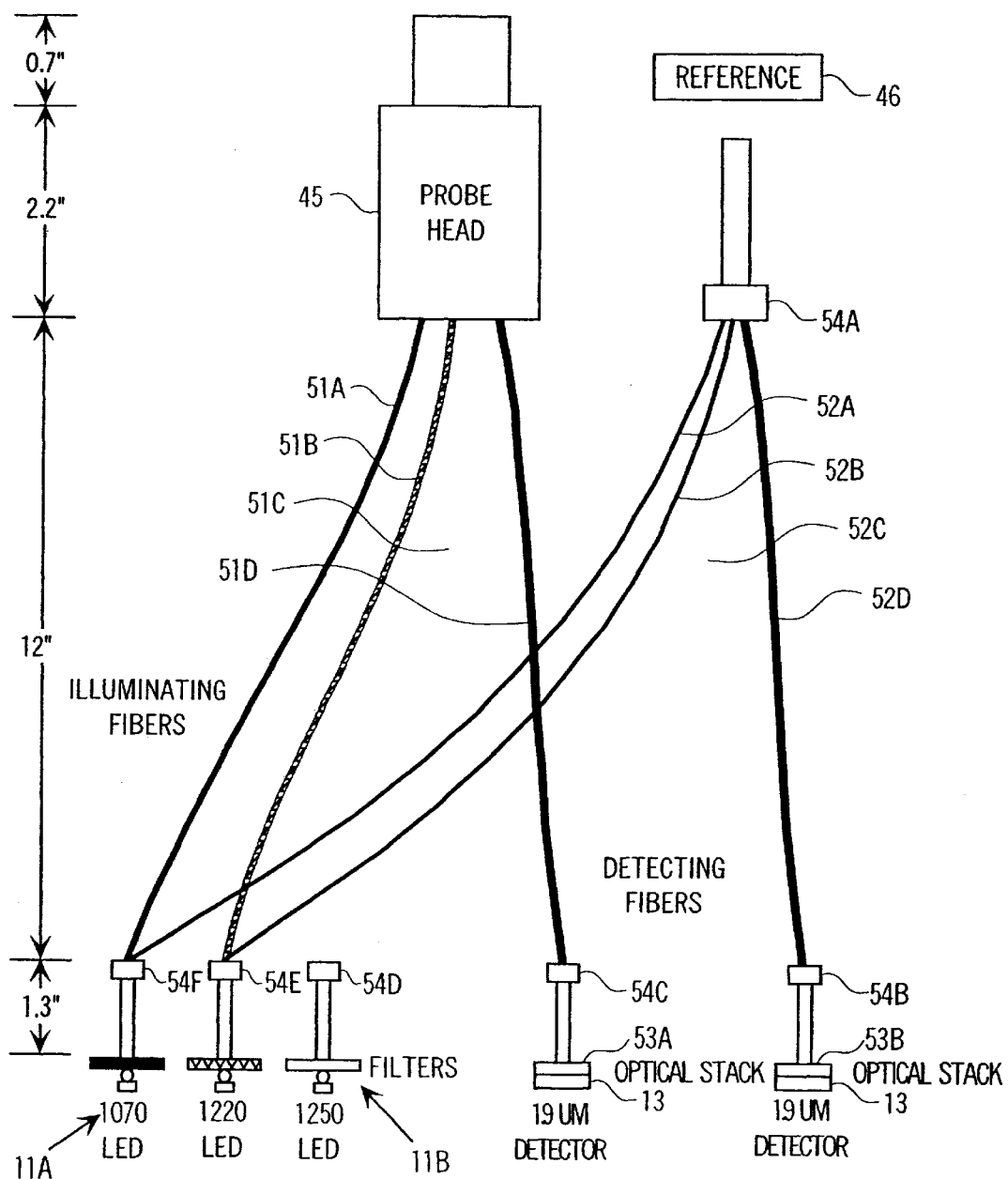
FIG. 4 illustrates an arrangement of illumination and detection fibers in the hydration meter of FIG. 3, according to the invention.

In the preferred embodiment, a group of LED's 11 is employed to transmit energy of pre-selected wavelengths to the skin; the LED's are radially surrounded by detection fibers 13 at specific distances. The LED's are alternately energized and the detected energy of each LED reflected or transmitted through the skin is used to form one spectrum. The edge-to-edge distance between each of the LED's and the detector elements, or the distance between the point of illumination, comprising the light-emitting surface of the LED's, and the point of detection is a minimum of 40 $\mu$m and a maximum of 1 mm. Distances of less than 40 $\mu$m produce too much surface reflection of the NIR radiation and distances of greater than 1 mm result in too much penetration of the NIR radiation. The set of wavelengths includes 1070, 1180, 1280 nm and 1110, 1190, and 1280 nm. However, other wavelength ranges, corresponding to water bands in the NIR absorbance spectrum are also suitable. Coupling of the illumination and detector elements, shown in detail in FIG. 4, is accomplished through fiber optics. One skilled in the art will appreciate that other coupling methods are suitable, including optics and lens systems, subject to the criterion for the distances between the point of illumination and detection. The detected intensity from the sample is converted to a voltage through analog electronics 14 and digitized through a 16-bit A to D converter (ADC) 15. The spectrum is passed to the hydration prediction procedure 16 for processing. First, the absorbance is calculated 17 on the basis of the detected light through—$\log(R/R_0)$ where R is the reflected light and $R_0$ is the light incident on the sample determined by scanning a reference standard. Subsequent processing steps, described below, result in either a hydration prediction or a message indicating an invalid scan. A block diagram of the integrated system is shown in FIG. 1.

Alternately, the measurement can be accomplished with existing NIR spectrometers that are commercially available, including a Perstorp Analytical NIRS 5000 spectrometer or a Nicolet Magna-IR 760 spectrometer. In addition, the measurement can be made by collecting reflected light off the surface of the skin or light transmitted through a portion of the skin, such as the finger or the ear lobe. Further, the use of reflectance or transmittance can replace the preferred absorbance measurement.

Hydration Prediction Procedure

The general procedure for quantifying hydration based on the measured spectrum, shown in FIG. 1, is implemented in a data processing system such as a microcomputer 44 that automatically receives the measurement information from the ADC 15. The hydration quantifying procedure comprises a series of steps, including outlier detection 18, preprocessing 19, and hydration prediction 20 wherein each step is a procedure in itself. Each procedure relies on a calibration set of exemplary measurements. Herein below, the general steps of the Hydration Prediction Procedure are summarized, with a detailed description following in the subsequent section titled "Implementation."

Measurement (17)

Figure 2:
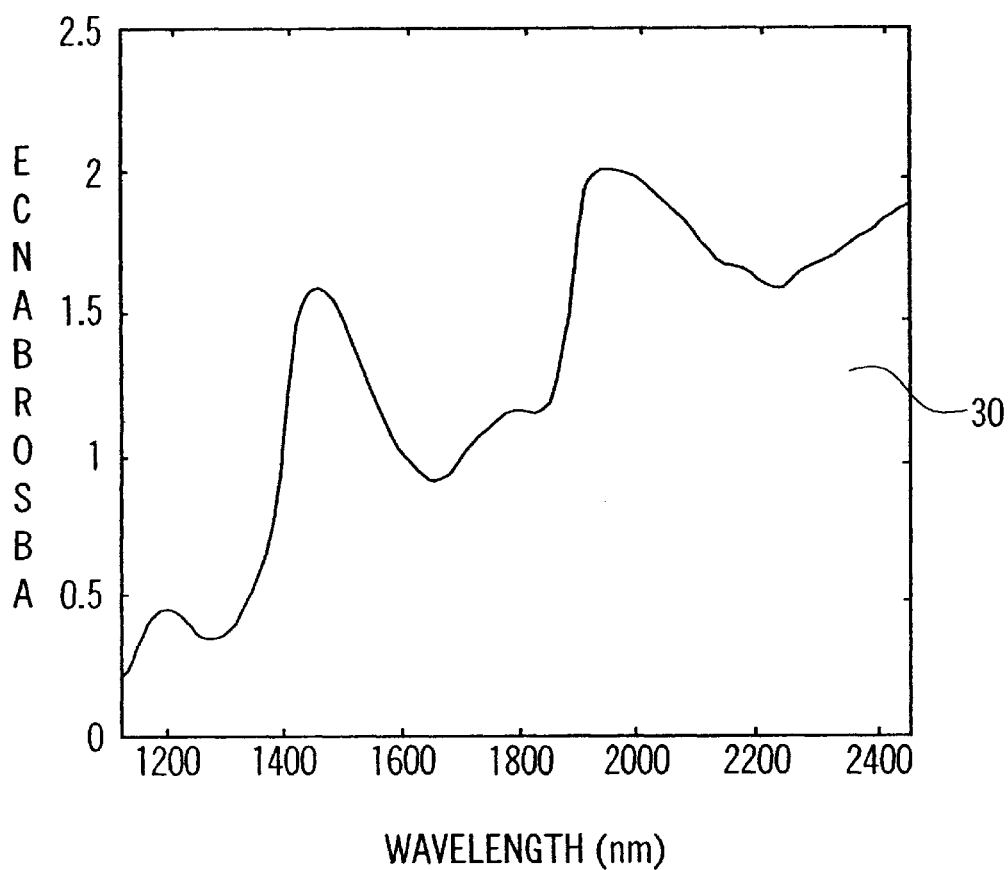
FIG. 2 illustrates a typical non-invasive NIR absorbance spectrum.

The measurement is a spectrum denoted by the vector $m \in \Re^N$ of absorbance values pertaining to a set of N wavelengths $\lambda \in \Re^N$ that span the near infrared (700 to 2500 nm). A typical plot 30 of m versus $\lambda$ is shown in FIG. 2.

Outlier Detection (18)

The outlier detection procedure provides a method of detecting invalid measurements through spectral variations that result from problems in the instrument, poor sampling of the subject or a subject outside the calibration set. The preferred method for the detection of spectral outliers is through a principal component analysis and an analysis of the residuals. See H. Martens, T. Naes, *Multivariate Calibration*, John Wiley & Sons, New York (1989). First, the spectrum, m, is projected onto five eigenvectors, contained in the matrix o, that were previously developed through a principal components analysis (on a calibration set of exemplary absorbance spectra) and are stored in the computer system of the device. The calculation is given by $$xpc_o = \sum_{k=1}^{5} m o_k \qquad (1)$$

and produces the 1 by 5 vector of scores, $xpc_o$, where $o^k$ is the $k^{th}$ column of the matrix o. The residual, q, is determined according to $$q = m - xpc_o o^T \qquad (2)$$

and compared to three times the standard deviation of the expected residual (of the calibration set). If greater, the sample is reported to be an outlier and the hydration measurement procedure is terminated.

Preprocessing (19)

Preprocessing includes operations such as scaling, normalization smoothing, derivatives, filtering and other transformations that attenuate the noise and instrumental variation without affecting the signal of interest. The preprocessed measurement, $x \in \Re^N$, is determined according to $$x = h(e,m) \qquad (3)$$

where $h: \Re^{N \times 2} \to \Re^N$ is the preprocessing function.

Prediction (20)

Prediction may include operations such as multiple linear least squares regression (MLR), principle component regression (PCR), and partial least squares regression (PLR) analysis that process the measurement, $y \in \Re^N$, according to $$y = g(x) \qquad (4)$$

where $g: \Re^N \to \Re^1$ is the regression function.

Implementation Details

This section describes a particular embodiment of the apparatus and specific procedures for quantifying SC hydration. The structure of the procedures relies on a priori knowledge of the systematic variation of the skin structure, namely, the hydration state of the stratum corneum and the variation in path depth of the irradiated light. However, the parameters of each procedure, such as the eigenvectors for outlier detection, are determined on the basis of an experimental data set providing exemplary information.

Apparatus

Figure 3:
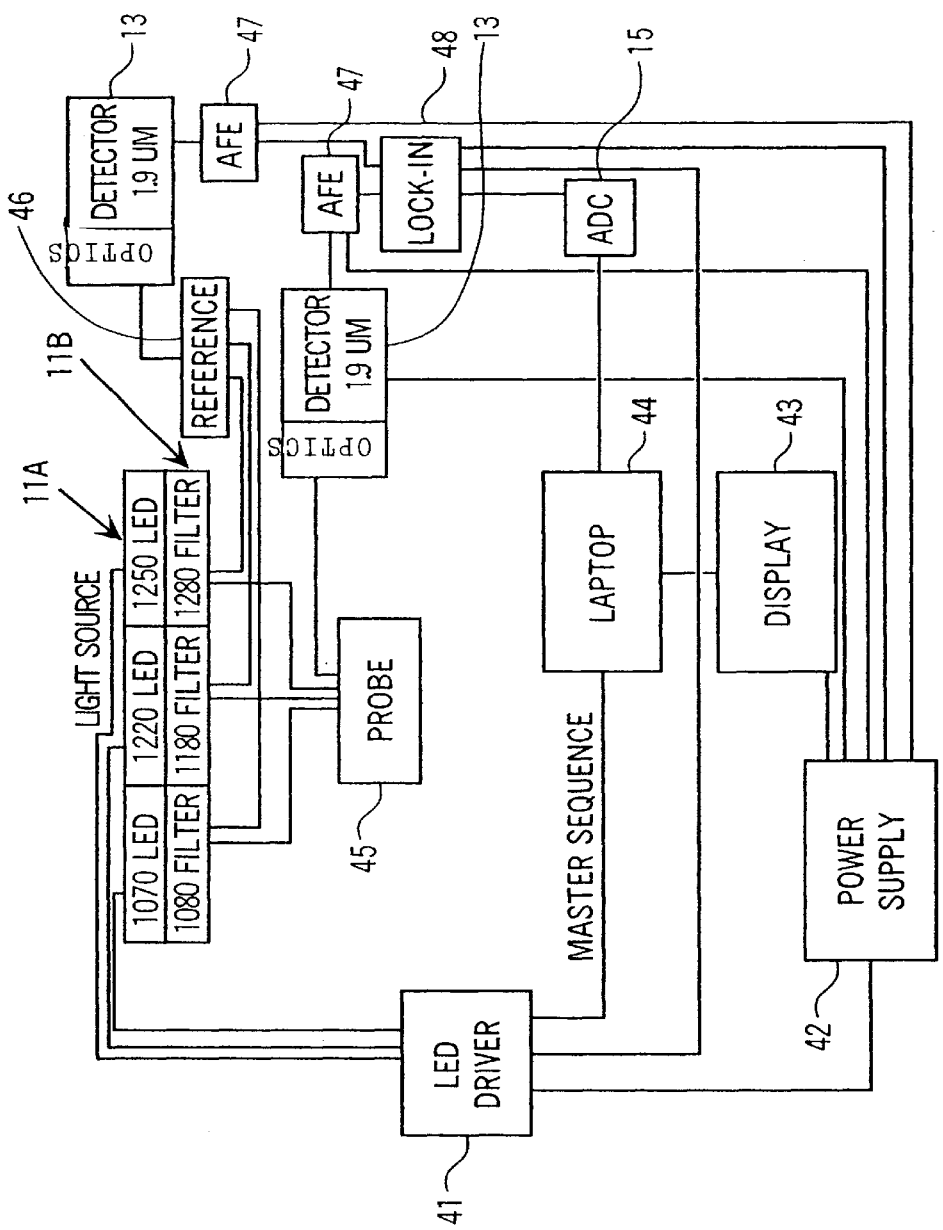
FIG. 3 provides a block diagram of a hydration meter, according to the invention.

FIG. 3 provides a block diagram for the hydration meter 40. The light source 11 for this device includes an array 11a of three light emitting diodes (LED's). The current source for the LED's is an LED driver 41 connected to a power supply 42 that pulses the LED's at a frequency of between 1 kHz and 10 kHz. The LED driver 41 supplies a current of up to 3.0 amperes. The LED's used for this device have a peak wavelength at 1.07 Ìm, 1.22 Ìm, and 1.25 Ìm. Each LED is equipped with a bandpass interference filter 11b; the bandpass interference filters of the preferred embodiment have center wavelengths of 1080 nm, 1180 nm, and 1280 nm, respectively, with their full width half maximum ranging from 11.0 to 14.8 nm. The light is transmitted to the probe heads 45, 46 via fiber optics 51a–c, 52a–c. FIG. 4 illustrates the coupling of the LED's 11a with the probe heads 45, 46 by means of fiber optics 51a–c, 52a–c.

Figure 5:
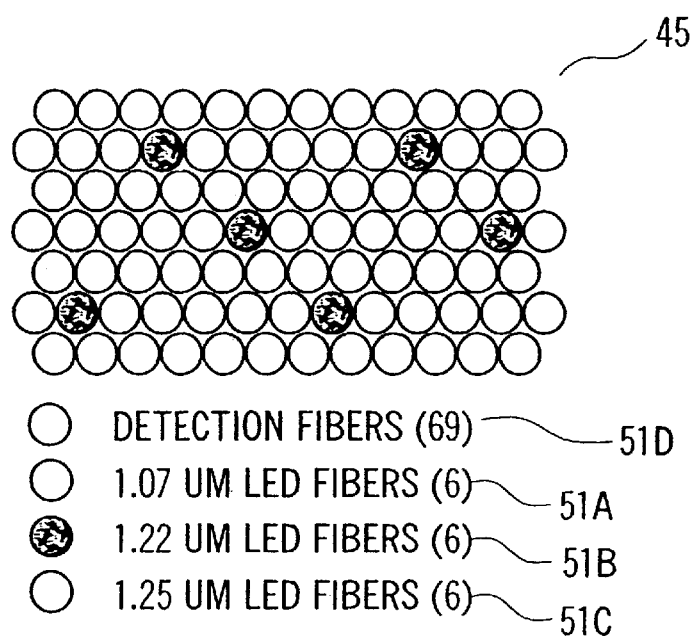
FIG. 5 illustrates an arrangement of illumination and detection fibers in a sample probe head of the hydration meter of FIG. 3, according to the invention.

Each LED has seven 100 Ìm core diameter fiber optics associated with it. Six of these fiber optics 51a–c go to the sample probe head 45, and one 52a–c goes to the reference probe head 46. The sample probe head 45 is the subject interface 12 of the device that comes into contact with the stratum corneum. FIG. 5 shows a preferred fiber optic arrangement for the sample probe head 45, comprising a total of eighteen illuminating fibers 51a–c and sixty-nine detecting fibers 51d. Each illuminating fiber 51a–c is completely surrounded, in a closed, packed arrangement, by detection fibers 51d for greatest light collection. Shown in FIG. 6, the reference probe head 46 is used to collect a dual beam reference of an internal diffuse reflectance standard having known spectral characteristics. The reference probe has a total of three illuminating fibers 52a–c and from 20 to 30 detecting fibers 52d. The diffuse reflected light from each of the probe heads, sample and reference, travels via optical fibers 51d, 52d to an optical system 53a, b that focuses the light onto the 1.9 Ìm InGaAs detectors 13. The fiberoptics are coupled to the various components with connecting elements 54a–f. In the preferred embodiment of the invention, the connecting elements 54 are brass connectors, but other equally suitable alternatives will be apparent to those skilled in the art.

The signals from the detectors are amplified in the analog front end 47 (AFE). The AFE also converts the current signal from the detectors to a voltage signal before transmitting the signal to the lock-in amplifier 48. The phase modulating lock-in amplifier 48 receives the signal from the AFE 47 and a reference signal from the LED driver 41. The lock-in amplifier 48 amplifies signals that are in phase with the reference signal. This increases the signal-to-noise ratio, and gives a direct current output. The output from the lock-in amplifier 48 goes through a 16-bit analog to digital converter (ADC) 15.

A laptop computer 44 or other data processing device receives the signal from the ADC 15, and predicts the hydration based on the invented algorithm 16 described further below. After the signal is processed, the prediction result is displayed on a display device 43 attached to the laptop 44 or other data processing device. The laptop also controls the master sequence 49 on the LED's. The laptop controls which LED is emitting and the time period for which each LED is emitting.

SC Hydration Prediction

The preferred analytical method for hydration prediction according to the invention is Multiple linear regression (MLR); the prediction calculation is given by:

$$\hat{y} = \hat{a}_1 x_1 + \hat{a}_2 x_2 + \hat{a}_3 x_3 + \hat{a} \quad (5)$$

where $\hat{y}$ is the predicted hydration; $x_1$, $x_2$, and $x_3$ are the absorbance of each LED, $\cdot_1$, $\cdot_2$, and $\cdot_3$ are the coefficients to the absorbance of each LED, and $\hat{A}$ is the error associated with the model. The coefficients are calculated by $$w = (x^t \cap x)^{-1} \cap x^t \cap y \quad (6)$$

where x is the matrix of absorbance values after the preprocessing techniques are complete, y is the corneometer readings for each spectral measurement, and w is the matrix containing the coefficients:

$$w = \begin{matrix} \hat{a}_1 \\ \hat{a}_2 \\ \hat{a}_3 \end{matrix} \quad (7)$$

Absorbance is calculated 17 by:

$$m = -\log \frac{R}{R_o} \quad (8)$$

where m is the absorbance spectrum, R is the intensity signal from the sample probe head, and $R_0$ is the intensity signal from the reference probe head. The absorbance spectrum, m, is passed through the outlier detection system 18 to remove any bad measurements or readings outside the prediction model's range. After outlier detection, the signal is preprocessed 19 to attenuate any noise and instrumental variation. The preprocessing techniques employed are multiplicative scatter correction and mean centering. The spectrum is processed, using multivariate scatter correction through a rotation that fits it to the expected or reference spectrum $\bar{n}$, determined from the calibration set. See P. Geladi, D. McDougall, H. Martens, *Linearization and Scatter-Correction for Near-infrared Reflectance Spectra of Meat*, Applied Spectroscopy, Vol. 39, pp. 491–500 (1985). First, the spectrum is fitted via linear regression according to $$m = a + b\bar{m} + e \quad (9)$$

where a and b are the slope and intercept and e is the error in the fit. The spectrum is then corrected through:

$$x = \frac{m-a}{b} \quad (10)$$

where x is the processed absorbance spectrum. From this spectrum, the mean from an exemplary data set is calculated for each LED absorbance. The mean is then subtracted from each LED absorbance in the measured data set. After mean centering the data, it is passed through the multiple linear regression model for the prediction of SC hydration. For the current embodiment, the coefficients for the multiple regression model, $\cdot_1$, $\cdot_2$, and $\cdot_3$, are 2411.4, −2486.6, and 257.2, respectively.

Other methods of developing a prediction model for the hydration of the stratum corneum may be used, for example, using factor analysis to develop a set of abstract features capable of representing the spectral variation related to hydration. For factor analysis, the spectral measurements, NIR absorbance spectra similar to that of FIG. 2, are used. The spectrum is sub-divided into one or more regions according to wavelength (wavelength selection) and is preprocessed and normalized to enhance spectral variation related to SC hydration. The measurements are projected onto one or more sets of previously determined factors (eigenvectors) to determine the scores. The scores constitute the extracted features and are subjected to a prediction procedure, such as linear discriminate analysis, SIMCA, k nearest-neighbor, fuzzy classification and various forms of artificial neural networks to predict hydration of the stratum corneum. See R. Duda, P. Hart, *Pattern Classification and Scene Analysis*, John Wiley & Sons, New York (1973) or S. Wold, M. Sjostrom, *SIMCA: A method for analyzing chemical data in terms of similarity and analogy*, Chemometrics: Theory and Application, ed. B. R. Kowalski, ACS Symposium Series, Vol. 52 (1977) or J. Bezdek, S. Pal, eds., *Fuzzy Models for Pattern Recognition*, IEEE Press, Piscataway, N.J. (1992) or J. Keller, M. Gray, J. Givens, *A fuzzy k nearest neighbor algorithm*, IEEE Transactions on Systems, Man, and Cybernetics, Vol. SMC-15(4), pp. 580–585, (July/August, 1985) or Y. Pao, *Adaptive Pattern Recognition and Neural Networks*, Addison-Wesley Publishing Company, Reading, Mass. (1989).

Experimental Data Set

A study was performed to develop a model for predicting SC hydration. The spectroscopic measurements were made using a spectrometer instrument according to an embodiment of the invention, comprising a quartz lamp, a monochromator, a fiber optic probe, and a detector set-up. The study consisted of four human subjects (3 males and 1 female), in which the hydration of the SC at the measurement site was modified by occluding the skin. Different occlusion times were employed to develop a range of hydration values, with no treatment of the skin at the sampling site prior to measurement. Stratum corneum hydration was measured independently by the corneometer CM 825, produced by Courage & Khazaka of Cologne, Germany. Each subject had a minimum of eight spectral scans with corresponding corneometer readings over a period of at least two days in duration, each scan constituting a sample. The spectral measurements and the corresponding corneometer readings are referred to as the "Experimental Data Set" herein below.

Feasibility

Figure 6:
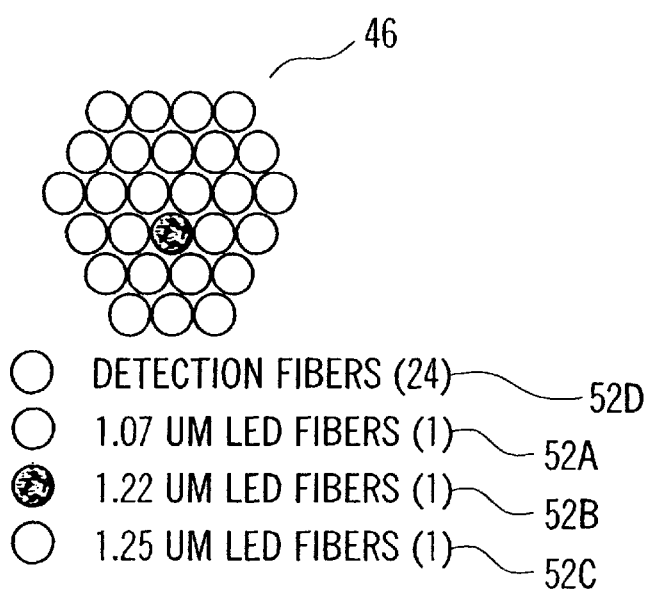
FIG. 6 illustrates an arrangement of illumination and detection fibers in a reference probe head of the hydration meter of FIG. 3, according to the invention.
Figure 7:
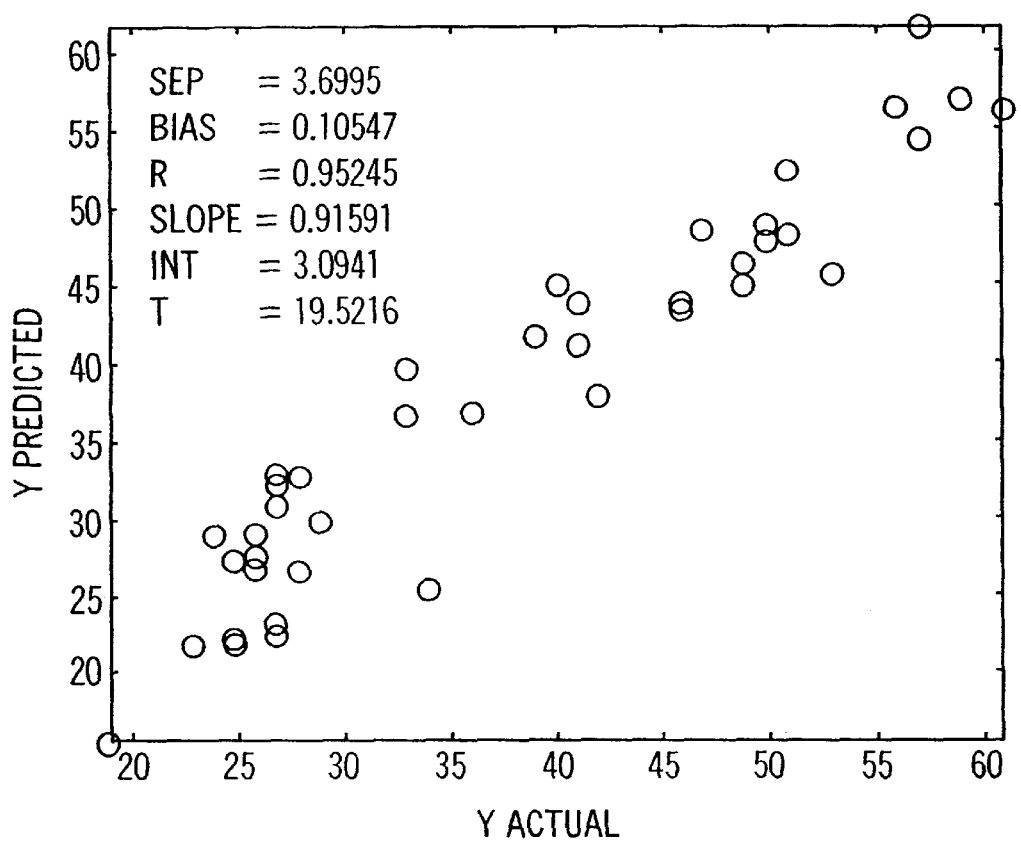
FIG. 7 shows a plot of actual SC hydration measurements vs. predictions in a calibration model for predicting SC hydration, according to the invention.
Figure 8:
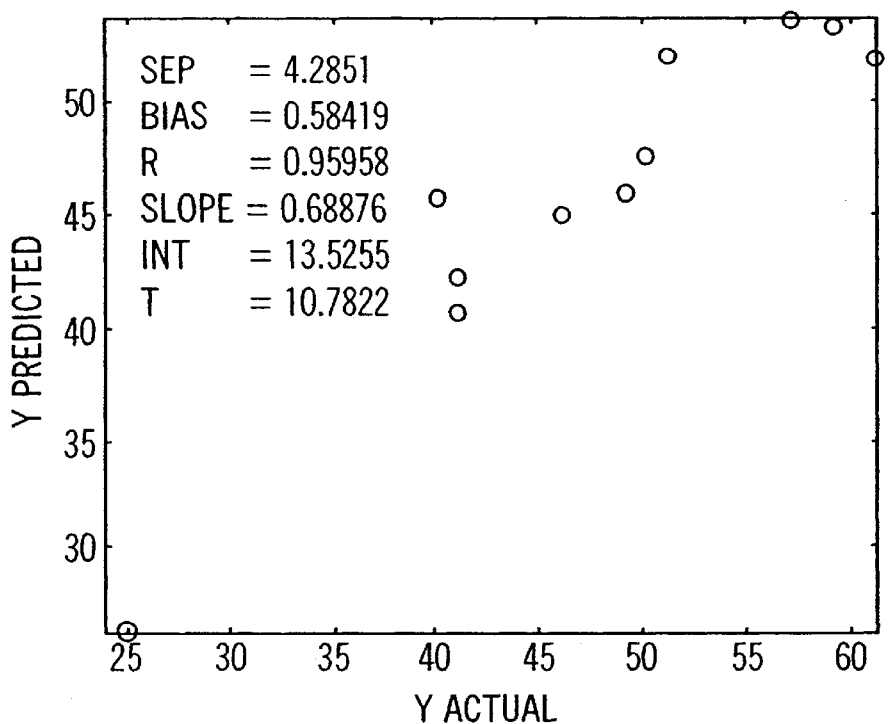
FIGS. 8 and 9 show plots of actual SC hydration measurements vs. predicted for two different subjects, based on the calibration model of FIG. 7, according to the invention.
Figure 9:
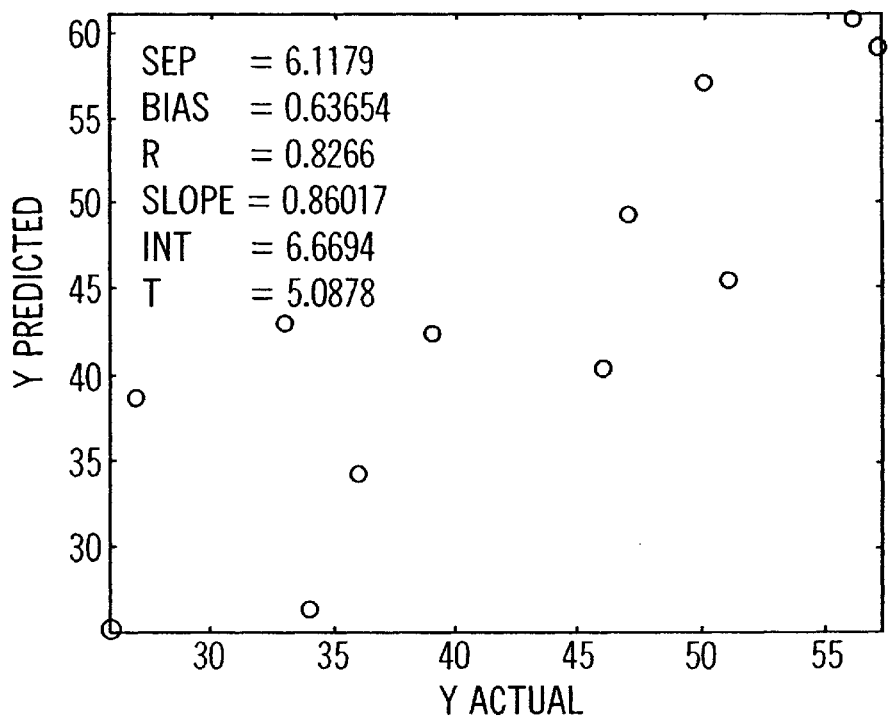

To demonstrate feasibility of the invented apparatus and method, the Experimental Data Set was analyzed using the previously described procedures. Outliers were removed using the outlier detection procedure previously described. Subsequently the data were preprocessed using MSC, followed by mean centering based on the mean of the emitting region of the filters based on their full width half maximum characteristics. The regions used were 1073–1087, 1175–1185, and 1275–1285 nm. Finally, MLR was applied to the data set. The calibration model was first developed using the samples of all four subjects, and subsequently validated using a "leave five out" cross-validation strategy. FIG. 6 shows a plot of actual corneometer measurements vs. predictions for the entire experimental data set. The standard error of prediction (SEP) for the experimental data set was 3.6995. Subsequently, a calibration model was developed and validated by using three subjects to develop the calibration model, and using the resulting model to predict SC hydration for the samples of the remaining subject. FIGS. 8 and 9 show plots of actual corneometer measurements vs. predictions for subjects four and three, respectively. The SEP was 4.2851 for subject four predictions and 6.1179 for subject three measurements.

Although the invention as described herein above utilizes three wavelength regions, one skilled in the art will recognize that that a different number of wavelength regions and specific wavelengths can be utilized, depending upon the requirements of the measurement. For example, an improvement in measurement accuracy can be achieved through the addition of more wavelength regions in the 1400–1500 nm and 1900–2500 nm regions.

Furthermore, the invention as described specifies particular wavelength regions for the measurement of tissue hydration. However, other spectral regions may be selected, in which absorbance due to water is present. For example, tissue hydration can be measured using ranges of 1400–1550 nm, 1720–1850 nm and 1900–2050 nm.

Finally, while the invention has been described in relation to the Stratum Corneum, hydration of the epidermis, the dermis and deeper tissue regions can be measured in the same manner as described by adjusting the illumination-to-detection distance according to the targeted depth of penetration.

Although the invention has been described herein with reference to certain preferred embodiments, one skilled in the art will readily appreciate that other applications may be substituted for those set forth herein without departing from the spirit and scope of the present invention. Accordingly, the invention should only be limited by the Claims included below.

What is claimed is:

1. A method for quantifying hydration of living tissue non-invasively, based on in vivo spectral measurements, comprising the steps of:
   providing a calibration set of exemplary samples and independent measurements, wherein a prediction model is developed from said calibration set;
   measuring a spectrum at a selected tissue measurement site on a living subject;
   estimating hydration of said tissue measurement site from said spectrum according to said prediction model.

2. The method of claim 1, wherein said spectral measurements comprise NIR spectra.

3. The method of claim 1, wherein said measurements are made using any of transmissive, diffuse reflectance and other methods, and wherein parameters for said method are determined based on information provided by said calibration set.

4. The method of claim 1, wherein said spectrum is denoted by a vector $m \in \Re^N$ of absorbance values pertaining to a set of N wavelengths $\lambda \in \Re^N$ spanning a wavelength region of approximately 700 to 2500 nm.

5. The method of claim 1, further comprising the step of:
   detecting outliers, wherein said outliers comprise invalid measurements.

6. The method of claim 5, wherein said invalid measurements result from any of instrument problems, poor sampling technique, and subjects outside of the calibration data set.

7. The method of claim 5, wherein said outlier detection step comprises the steps of:
   performing a principal components analysis (PCA) of said measured spectrum; and
   analyzing resulting residuals.

8. The method of claim 7, wherein said PCA comprises projecting said measured spectrum m onto five eigenvectors contained in a matrix o that were previously developed through a PCA of absorbance spectra from said exemplary data set, wherein the calculation is given by:

$$xpc_o = \sum_{k=1}^{5} mo_k,$$

wherein a one by five vector of scores is produced, $xpc_o$, where $o_k$ is the $k^{th}$ column of the matrix o.

9. The method of claim 8, wherein residual, q, is determined according to:

$$q = m - xpc_o o^1$$

and compared to three times the standard deviation of an expected residual from said calibration set, and wherein, if greater, the measurement is reported as an outlier.

10. The method of claim 1, further comprising the step of preprocessing said measured spectrum.

11. The method of claim 10, said preprocessing step including transformations that attenuate noise and instrumental variation.

12. The method of claim 11, wherein said preprocessing transformations include any of: scaling, normalization, smoothing, and filtering.

13. The method of claim 11, wherein a preprocessed measurement is determined according to:

$$x = h(\ddot{e}m),$$

where $h: \Re^{N \times 2} \to \Re^N$ is a preprocessing function.

14. The method of claim 1, wherein said estimating step includes any of multiple least squares regression (MLR), principle component regression (PCR), and partial least squares regression (PLR) analysis wherein the measurement $y \in \Re^N$ is processed according to:

$$y = g(x),$$

where $g: \Re^N \to \Re^1$ is a regression function.

15. The method of claim 1, wherein said step of measuring a spectrum at a selected tissue measurement site on a living subject comprises:
   using an apparatus for measuring an NIR absorbance spectrum to measure said spectrum.

16. The method of claim 15, wherein said apparatus comprises an energy source, said energy source comprising a plurality of LED's, each of said LED's emitting energy at a different targeted wavelength within a wavelength range of approximately 700–2500 nm;
   a sample probe head, said sample probe head comprising a subject interface and being substantially in contact with said tissue measurement site and delivering NIR energy emitted by said energy source to said tissue measurement site; and a reference probe head, said reference probe head delivering NIR energy emitted by said energy source to an internal reference standard having known spectral characteristics.

17. The method of claim 16, wherein said tissue measurement site comprises an area of the skin of said living subject.

18. The method of claim 17, wherein the absorbance spectrum is calculated by:

$$m = -\log\frac{R}{R_o},$$

where m is the absorbance spectrum, and R is an intensity signal from said sample probe head, $R_0$ is an intensity signal from said reference probe head.

19. The method of claim 18, wherein said spectrum, m, is analyzed to detect outliers, said outliers comprising invalid measurements, or readings outside the range of said prediction model.

20. The method of claim 19, wherein said spectrum is preprocessed, said preprocessing step comprising:
multiplicative scatter correction (MSC), wherein said spectrum is processed through a rotation that fits it to a reference spectrum $\overline{m}$ determined from said calibration set; and
mean centering.

21. The method of claim 20, wherein said MSC step comprises the steps of:
fitting said spectrum via linear regression according to:

$$m = a + b\overline{m} + e,$$

where a and b are the slope and intercept and e is the error in fit; and
correcting said spectrum through:

$$x = \frac{m-a}{b},$$

where x is the preprocessed spectrum.

22. The method of claim 21, wherein said mean centering step comprises the steps of:
calculating a mean for each LED absorbance from said calibration set;
subtracting said mean from each LED absorbance in the measured spectrum.

23. The method of claim 17, wherein said prediction model is a multiple linear regression (MLR) model for predicting Stratum Corneum hydration.

24. The method of claim 23, wherein the prediction calculation is given by:

$$\hat{y} = \hat{a}_1 x_1 + \hat{a}_2 x_2 + \hat{a}_3 x_3 + \hat{a}, \tag{5}$$

where $\hat{y}$ is the predicted hydration; $x_1$, $x_2$, and $x_3$ are the absorbance of each LED, $\hat{a}_1$, $\hat{a}_2$, and $\hat{a}_3$ are the coefficients to the absorbance of each LED, and $\hat{a}$ is the error associated with the model.

25. The method of claim 24, wherein the coefficients are calculated by:

$$w = (x^T x)^{-1} x^T y,$$

where x is the matrix of absorbance values after the preprocessing techniques are complete, y is the independent measurements for each spectral measurement, said independent measurements comprising corneometer readings, and w is the matrix containing the coefficients:

$$w = \begin{matrix} \hat{a}_1 \\ \hat{a}_2 \\ \hat{a}_3 \end{matrix}.$$

26. The method of claim 1, wherein said prediction model includes a preprocessing algorithm.

27. The method of claim 1, further comprising the step of developing said prediction model using factor-based analytical methods, wherein a set of abstract features is developed that is capable of representing spectral variation related to tissue hydration.

28. The method of claim 27, wherein said developing step comprises the steps of:
providing NIR absorbance spectra;
selecting wavelengths from said spectra, wherein said spectra are sub-divided into one or more regions according to wavelength;
preprocessing and normalizing said spectra, wherein spectral variation related to tissue hydration is enhanced;
projecting said measurements onto one or more sets of previously determined factors, said factors comprising eigenvectors, to determine scores, wherein said scores constitute extracted features; and
subjecting said scores to a prediction procedure, said procedure comprising any of linear discriminant analysis, SIMCA, k nearest neighbor, fuzzy classification, an artificial neural networks.

* * * * *